(12) United States Patent
Michoux et al.

(10) Patent No.: US 10,609,880 B2
(45) Date of Patent: Apr. 7, 2020

(54) BIOREACTOR

(71) Applicant: Evonik Advanced Botanicals SAS, Evry (FR)

(72) Inventors: Franck Michoux, Amilly (FR); Marko Boehm, Schwesing (DE)

(73) Assignee: Evonik Advanced Botanicals SAS, Evry (FR)

( * ) Notice: Subject to any disclaimer, the term of this patent is extended or adjusted under 35 U.S.C. 154(b) by 291 days.

(21) Appl. No.: 15/526,876

(22) PCT Filed: Dec. 11, 2015

(86) PCT No.: PCT/EP2015/079490
§ 371 (c)(1),
(2) Date: May 15, 2017

(87) PCT Pub. No.: WO2016/092098
PCT Pub. Date: Jun. 16, 2016

(65) Prior Publication Data
US 2017/0318763 A1 Nov. 9, 2017

(30) Foreign Application Priority Data

Dec. 11, 2014 (GB) .................................. 1421992.7

(51) Int. Cl.
*A01G 31/02* (2006.01)
*A01H 4/00* (2006.01)
(52) U.S. Cl.
CPC ............. *A01G 31/02* (2013.01); *A01H 4/001* (2013.01); *Y02P 60/216* (2015.11)
(58) Field of Classification Search
CPC .... A01G 21/06; A01G 27/001; A01G 27/003; A01G 31/02; A01G 31/06; A01G 25/165; C12M 21/06; A01H 4/001
See application file for complete search history.

(56) References Cited

U.S. PATENT DOCUMENTS 3,339,308 A 9/1967 Clare
3,906,667 A * 9/1975 Williams ............... A01G 27/00
47/79

(Continued)

FOREIGN PATENT DOCUMENTS

AT 216808 T 5/2002
EP 2617282 A1 7/2013

(Continued)

OTHER PUBLICATIONS

International Search Report dated Mar. 22, 2016 in PCT/EP2015/079490 (3 pages).

(Continued)

*Primary Examiner* — Christopher D Hutchens
(74) *Attorney, Agent, or Firm* — Philip P. McCann; Nexsen Pruet PLLC

(57) ABSTRACT

A temporary immersion bioreactor (10) for in vitro production of differentiated plant biomass including a growth chamber (12) having one or more transparent side walls (14) and a mesh bottom (16), the mesh bottom (16) defining a plurality of pores (18) to receive plant material. The bioreactor (10) includes a flexible bag (20) formed from a transparent material, the flexible bag (20) having a sealable opening and being dimensioned to receive the growth chamber (12) together with a liquid medium (22). The bioreactor (10) also includes an outer chamber (24) having one or more transparent side walls (26). the outer chamber (24) is formed to correspond in shape to the growth chamber (12) and dimensioned to receive the growth chamber (12) within the flexible bag (20) so that the mesh bottom (16) of the growth chamber (12) faces a bottom (28) of the outer chamber (24) that in use is intended to rest on a support surface. Movement of the growth chamber (12) within the outer chamber (24) is restrained to movement along a single axis such that the mesh bottom (16) of the growth chamber (12) moves towards and away from the bottom (28) of the outer chamber (24).

21 Claims, 12 Drawing Sheets

(56) References Cited

U.S. PATENT DOCUMENTS

| | | | |
|---|---|---|---|
| 4,521,989 A | 6/1985 | Meyer | |
| 4,813,176 A | 3/1989 | Takayasu | |
| 5,094,030 A * | 3/1992 | Chia | A01G 31/02 47/14 |
| 5,896,701 A * | 4/1999 | Schaerer | A01G 31/02 206/815 |
| 2012/0297507 A1 | 11/2012 | Michoux et al. | |
| 2016/0130596 A1 | 5/2016 | Michoux et al. | |
| 2017/0002373 A1 | 1/2017 | Michoux et al. | |

FOREIGN PATENT DOCUMENTS

| | | |
|---|---|---|
| WO | 9422290 A1 | 10/1994 |
| WO | 9625484 A1 | 8/1996 |
| WO | 0164844 A1 | 9/2001 |
| WO | 2012044239 A1 | 4/2012 |
| WO | 2012146872 A1 | 11/2012 |

OTHER PUBLICATIONS

Written Opinion dated Mar. 22, 2016 in PCT/EP2015/079490 (6 pages).

\* cited by examiner

BIOREACTOR

This application is a national stage application under 35 U.S.C. § 371 of International Application No. PCT/EP2015/079490 filed 7 Dec. 2015, which claims priority to GB Application No. 1421992.7 filed 11 Dec. 2014, the disclosures of which are expressly incorporated herein by reference.

FIELD

The invention relates to a bioreactor for in vitro production of differentiated plant biomass, such as shoots or roots, by temporary immersion.

BACKGROUND

Conventional micropropagation to produce differentiated plant biomass is generally expensive and labor intensive. Various types of vessels have therefore been developed for in vitro culture of plants so as to overcome these issues. The methodologies used in these vessels can be divided roughly into four types: liquid-phase, gas-phase, hybrid bioreactors and temporary immersion systems (TIS).

A temporary immersion system is a periodic, semi-automated or fully automated cultivation system based on alternating cycles of temporary immersion of the cultured plant tissue into a liquid medium followed by draining and exposing the plant tissue to a gaseous environment. Usually the immersion period is relatively short, in the region of a few minutes, whereas the air exposure period is prolonged, in the region of several hours. By adjusting the duration of periods of immersion and exposure it is possible to create conditions for optimal humidity and supply nutrients with minimal liquid contact, thereby making it possible to reduce significantly the hyperhydricity of the cultured plant tissue.

As well as reducing hyperhydricity of the cultured plant tissue, temporary immersion systems are considered the best for the production of differentiated plant tissue because they produce more plants per square meter. They have higher multiplication rates and the use of a liquid medium reduces agar costs. Temporary immersion results in higher nutrient uptake and assimilation, and forced aeration increases growth and biomass production. Reduced manipulations and reduced labor costs are another advantage, together with improved plant quality and the production of higher fresh and dry weight yields.

SUMMARY

According to an aspect of the invention there is provided a temporary immersion bioreactor for in vitro production of differentiated plant biomass comprising:

a growth chamber having one or more transparent side walls and a mesh bottom, the mesh bottom defining a plurality of pores to receive plant material;

a flexible bag formed from a transparent material, the flexible bag having a sealable opening and being dimensioned to receive the growth chamber together with a liquid medium;

an outer chamber having one or more transparent side walls, the outer chamber being formed to correspond in shape to the growth chamber and dimensioned to receive the growth chamber within the flexible bag so that the mesh bottom of the growth chamber faces a bottom of the outer chamber and movement of the growth chamber within the outer chamber is restrained to movement along a single axis such that the mesh bottom of the growth chamber moves towards and away from the bottom of the outer chamber; and a driving mechanism arranged to selectively drive movement of the growth chamber along a single axis, when the growth chamber and flexible bag are received in the outer chamber, between a first position in which the mesh bottom of the growth chamber is located at or towards the bottom of the outer chamber and a second position in which the mesh bottom of the growth chamber is spaced from the bottom of the outer chamber.

It will be appreciated that, in use, the bottom of the outer chamber is intended to rest on a support surface.

DETAILED DESCRIPTION

A temporary immersion bioreactor for in vitro production of differentiated plant biomass comprising:

a growth chamber having one or more transparent side walls and a mesh bottom, the mesh bottom defining a plurality of pores to receive plant material;

a flexible bag formed from a transparent material, the flexible bag having a sealable opening and being dimensioned to receive the growth chamber together with a liquid medium;

an outer chamber having one or more transparent side walls, the outer chamber being formed to correspond in shape to the growth chamber and dimensioned to receive the growth chamber within the flexible bag so that the mesh bottom of the growth chamber faces a bottom of the outer chamber that in use is intended to rest on a support surface and movement of the growth chamber within the outer chamber is restrained to movement along a single axis such that the mesh bottom of the growth chamber moves towards and away from the bottom of the outer chamber; and a driving mechanism arranged to selectively drive movement of the growth chamber along a single axis, when the growth chamber and flexible bag are received in the outer chamber, between a first position in which the mesh bottom of the growth chamber is located at or towards the bottom of the outer chamber and a second position in which the mesh bottom of the growth chamber is spaced from the bottom of the outer chamber.

When the flexible bag containing a liquid medium and the growth chamber is located in the outer chamber, the liquid medium will inevitably collect at the bottom of the flexible bag, adjacent the bottom of the growth chamber. Accordingly the provision of a driving mechanism to selectively drive movement of the growth chamber along the single axis between the first and second positions in the outer chamber allows temporary immersion of the growth chamber in the liquid medium.

The use of a driving mechanism to effect temporary immersion of the growth chamber is advantageous because it readily allows the bioreactor to be scaled up to operate on a relatively large scale.

In use the first position of the mesh bottom of the growth chamber must be sufficiently close to the bottom of the outer chamber so as to immerse the pores of the mesh in the liquid medium contained in the flexible bag at the bottom of the outer chamber. It will be appreciated therefore that in this first position the mesh bottom need not be located exactly at the bottom of the outer chamber. It may be spaced from the bottom of the outer chamber.

In the second position the mesh bottom must be moved away from the bottom of the outer chamber so as to lift the mesh bottom of the growth chamber out of the liquid medium. The exact locations of the first and second positions will therefore depend on the depth of the liquid medium which collects in the flexible bag at the bottom of the outer chamber. It will however be appreciated that the mesh bottom in the second position will be spaced further from the bottom of the outer chamber than it is when it is located in the first position.

The mesh bottom of the growth chamber readily allows ingress of the liquid medium into the growth chamber as the growth chamber is moved to the first position and immersed in the liquid medium. Similarly the mesh bottom allows the liquid medium to drain from the growth chamber as the growth chamber is moved to the second position and removed from the liquid medium. Accordingly the use of a mesh bottom allows an efficient flow of liquid medium into and out of the pores.

In conventional bioreactors using temporary immersion, the liquid medium is moved onto the plant material so as to immerse the plant material. The liquid medium is moved either mechanically or by air pressure, using an air compressor for example. Not only does such an approach introduce the risk of the liquid medium overflowing from the support holding the plant material and thereby the risk of plant material being washed out of the support, but the relatively high-pressure, high-energy demand needed to circulate the liquid medium in such methodologies renders it impractical to scale-up the size and capacity of the bioreactors. Accordingly conventional bioreactors using temporary immersion can only operate on a laboratory scale, typically being limited to a maximum volume of 10 liters, and do not allow temporary immersion to be used to produce differentiated plant biomass on a commercial scale.

In contrast, the applicant has discovered that driving movement of the relatively light growth chamber so as to immerse plant material contained in the growth chamber in a liquid medium requires significantly less energy and thus allows the size and capacity of the bioreactor to be scaled up to a maximum volume in the range of 10-1,000 liters, and preferably a maximum volume in the range of 30-150 liters.

The use of a flexible bag to sealably contain the growth chamber and, in use, the liquid medium, not only prevents the ingress of contaminants into the liquid medium but also further facilitates scaling up of the bioreactor. The use of a flexible bag may, for example, allow the capacity of the bioreactor to be scaled up to 2,000 liters.

The use of transparent materials to form the growth chamber, the flexible bag and the outer chamber allows light to penetrate and reach plant material located in the pores of the mesh bottom of the growth chamber.

The growth chamber and the outer chamber each have at least one transparent wall so as to allow light to penetrate into the growth chamber and the outer chamber. In embodiments of the invention, it is envisaged that the other walls of the chamber may be formed from a solid or opaque material in order to control the amount of light that is able to penetrate into the growth chamber and the outer chamber. In particularly preferred embodiments however all of the walls of the growth chamber and the outer chamber are formed from a transparent material so as to allow a maximum amount of light to penetrate into the growth chamber and the outer chamber.

The number of walls of the growth chamber and the outer chamber will of course depend on the shape of the chambers. In circumstances where the chambers are circular or elliptical in shape, only one wall will be required. In order to create chambers having other shapes, the chambers may have two, three, four, five or more interconnected walls.

The provision of an outer chamber to receive the growth chamber sealed in the flexible bag with liquid medium reduces voids in the liquid medium and limits movement of the growth chamber so as to allow movement in use along the single axis only, into and out of the liquid medium.

In particularly preferred embodiments of the invention, the single axis along which the growth chamber moves into and out of the liquid medium will be essentially vertical. In other embodiments however it is envisaged that the single axis might extend at an angle to the vertical, the only requirement being that movement of the growth chamber along the axis moves the mesh bottom of the growth chamber towards and away from the bottom of the outer chamber.

Gas may be sealed in the flexible bag so that plant material contained in the growth chamber is exposed to the gas when it is moved to the second position and removed from the liquid medium.

Preferably the flexible bag includes a sealable port to receive liquid medium and/or inoculum. It will be appreciated that liquid medium and inoculum may be introduced into the bioreactor via the sealable port at the same time or separately, depending on the circumstances. It is not therefore essential that liquid medium and inoculum are introduced into the bioreactor via the sealable port at the same time.

The provision of a sealable port, typically having a diameter in the range of 0.5-5 cm, readily allows the introduction of liquid medium and inoculum, as required, into the flexible bag. It also allows the risk of contamination to be minimised whilst allowing scaling up of the size and capacity of the bioreactor. This is because only the sealable port need be located within a sterile environment during the introduction of liquid medium and/or inoculum into the flexible bag as opposed to the entire bioreactor.

It will be appreciated that contamination would waste any plant material contained in the bioreactor. Accordingly, the ability to effectively prevent the ingress of contaminants is particularly important when considering the scaling up in size and capacity of the bioreactor. The greater the capacity of the bioreactor the greater the amount of plant material that would be wasted in the event of contamination.

In the absence of the port to introduce liquid medium and/or inoculum it would be necessary to re-open the sealable opening of the flexible bag in order to introduce and replenish the liquid medium and/or introduce inoculum. Accordingly, in order to avoid contamination, it would be necessary for at least the entire opening and very likely the entire bioreactor to be located in a sterile environment. The sterile environment is typically provided through the use of a laminar flow hood. It will be appreciated therefore that, in such arrangements, the size of the laminar flow hood would limit the maximum size and capacity of the bioreactor.

Such limitations do not exist when a sealable port is provided to introduce liquid medium and/or inoculum. This is because, once the growth chamber is located inside the flexible bag on initial set up of the bioreactor, it is not necessary to re-open the sealable opening of the flexible bag. Accordingly, as outlined above, only the sealable port need be located in the sterile environment to prevent the ingress of contaminants when introducing liquid medium and/or inoculum into the bioreactor, and the remainder of the bioreactor may be located outside of the sterile environment.

In preferred embodiments, the bioreactor may further include an air pump for connection to the flexible bag so as to allow a gas to be conveyed through the flexible bag. The creation of a flow of gas through the flexible bag, in use, improves aeration of plant material located in the pores of the mesh bottom of the growth chamber when the growth chamber is removed from the liquid medium.

In such embodiments the flexible bag preferably includes at least three ports, first and second ports being configured for connection to the air pump to allow the flow of gas into and out of the flexible bag whilst the third port is configured to receive the liquid medium and inoculum therethrough.

The driving mechanism provided to drive movement of the growth chamber may include a drive arm located within the outer chamber so as to engage an underside of the mesh bottom of the growth chamber, via the flexible bag, when the growth chamber and flexible bag are received in the outer chamber. The drive arm in such embodiments is movable in a first direction along the single axis upwards from the bottom of the outer chamber to an extended position so as to push the growth chamber from the first position to the second position. The drive arm is movable from this extended position in a second, opposite direction along the single axis so as to guide movement of the growth chamber downwards from the second position to the first position.

It will be appreciated that in such embodiments the drive arm does not engage the entire underside of the mesh bottom of the growth chamber so as to allow liquid medium to drain from the growth chamber into pockets in the flexible bag formed on opposite sides of the drive arm as the drive arm moves upwards, towards the extended position, to drive movement of the growth chamber from the first position to the second position.

On downward movement of the drive arm, the pockets in the flexible bag on each side of the drive arm reduce in depth until the growth chamber reaches the first position at the bottom of the outer chamber and is immersed in liquid medium collected in the flexible bag, above the drive arm, across the entire width of the outer chamber.

Whilst a vacuum pump may be used to drive movement of the drive arm, vacuum pumps are energy intensive and greatly increase power consumption on scaling up of the bioreactor. In preferred embodiments therefore one or more electric motors are used to drive movement of the drive arm and thereby drive movement of the growth chamber.

In other embodiments the driving mechanism may include a float element mounted so as to extend around the mesh bottom of the growth chamber and thereby allow the growth chamber to float on a liquid medium contained in the flexible bag when the growth chamber and flexible bag are received in the outer chamber and thereby locate the growth chamber in the second position.

So as to immerse the growth chamber in the liquid medium when required, the driving mechanism in such embodiments further includes one or more drive elements provided in the outer chamber to selectively engage the growth chamber and drive movement of the growth chamber downward from the second position to the first position.

The float element may have a depth of at least 5 cm such that it protrudes at least 5 cm beneath the mesh bottom of the growth chamber so that, when the growth chamber floats on a liquid medium, the mesh bottom of the growth chamber is spaced at least 5 cm from the surface of the liquid medium. Spacing the mesh bottom from the surface of the liquid medium when the growth chamber is in the second position is advantageous in that it reduces the risk of plant roots or shoots protruding below the mesh bottom remaining immersed in the liquid medium.

In particularly preferred embodiments the float element has a depth of 10 cm.

In other embodiments the driving mechanism may include at least two electro-magnets to locate the growth chamber in the second position. In such embodiments at least two electro-magnets may be located within the outer chamber, towards the bottom of the outer chamber, and at least two electro-magnets located on an external surface of the growth chamber, in the vicinity of the mesh bottom of the growth chamber. In such embodiments the electro-magnets are selectively operable so as to create opposing magnetic fields. The creation of opposing magnetic fields serves to drive movement of the growth chamber in the first direction along the single axis, upwards from the first position to the second position.

As with embodiments in which the driving mechanism includes a float member, the driving mechanism in such embodiments further includes one or more drive elements provided in the outer chamber to selectively engage the growth chamber and drive movement of the growth chamber downward from the second position to the first position when immersion of the growth chamber in the liquid medium is required.

In embodiments where the driving mechanism includes a float member or opposing electro-magnets to maintain the growth chamber in the second position, the or each drive member provided to drive movement of the growth chamber downward when immersion in the liquid medium is required may be provided in the form of a plunger located within the outer chamber. The or each plunger has an engagement member to engage an upper edge of the or at least one side wall of the growth chamber, via the flexible bag, when the growth chamber and the flexible bag are received in the outer chamber. The or each plunger is movable to drive movement of the respective engagement member along the single axis downwards from the top of the outer chamber, from a rest position to an extended position, and thereby drive movement of the growth chamber from the second position to the first position. The or each plunger is movable to drive movement of the respective engagement member from this extended position in a second, opposite direction along the single axis so as to guide movement of the growth chamber upwards from the first position to the second position under the action of the float member or opposing electro-magnets.

Preferably, in such embodiments, the driving mechanism includes at least three such plungers located within the outer chamber at equidistantly spaced locations about an inner circumference of the outer chamber. Such an arrangement allows the driving mechanism to apply a downward driving force equally at spaced locations about the growth chamber and thereby reduces the risk of a turning force being applied to the growth chamber, which could otherwise prevent smooth downward movement of the growth chamber within the outer chamber.

In such embodiments, each of the plungers may be housed within a sealed plunger housing and driven by changes in pressure in a fluid contained within the housing so as to act on an end of the plunger and thereby drive movement of the plunger out of the housing on an increase in pressure and cause retraction of the plunger on a decrease in pressure.

In other such embodiments, each of the plungers may be driven by means of an electric motor.

In other embodiments where the driving mechanism includes a float member to maintain the growth chamber in the second position, the driving mechanism may also include electro-magnets to drive movement of the growth chamber downward when immersion in the liquid medium is required. In such embodiments at least two electro-magnets may be located within the outer chamber, towards the bottom of the outer chamber, and at least two electro-magnets located on an outer surface of the growth chamber, in the vicinity of the mesh bottom of the growth chamber. The electro-magnets are selectively operable so as to create attractive magnetic fields and thereby drive movement of the growth chamber in the second direction along the single axis, downwards from the second position to the first position. On removal of the attractive magnetic fields, by switching off the electro-magnets, the float member causes upward movement of the growth chamber from the first position to the second position.

It will be appreciated that in each of the embodiments referred to above, the driving mechanism preferably includes a timer to control activation and deactivation of the drive arm, the electro-magnets and/or the plunger(s) and thereby, in use, control movement of the growth chamber between the first and second positions. By appropriate setting of the timer, it is possible to set specific periods of immersion and aeration as may be required for a particular plant material located in the pores of the mesh bottom of the growth chamber.

So as to ensure effective operation, the flexible bag is preferably formed from a flexible thermoplastic polymer such as polypropylene, polyethylene and polyurethane, for example. It is also envisaged that other polymeric materials suitable for forming a transparent sheet of flexible material may also be used to form the flexible bag.

The growth and outer chambers may be manufactured by moulding or shaping a transparent plastics material into its final form, the plastics material being chosen from synthetic or natural polymers. In other embodiments the growth and outer chambers may be manufactured from a transparent resin using a 3D printer.

It is envisaged that other materials could be used to make one of the component parts, or all of the component parts, of the bioreactor. For example, to improve the environmental friendliness of the bioreactor, appropriate biodegradable or recyclable materials could be used.

So as to allow the outer chamber to guide movement of the growth chamber effectively in use, the cross-sectional shapes of the growth chamber and the outer chamber, in a plane generally perpendicular to the single axis, are the same. Provided the cross-sectional shape of the two chambers is the same, the chambers may be formed to define any cross-sectional shape including, for example, circular, elliptical, square, triangular or rectangular.

It will be appreciated that in embodiments where the growth chamber and the outer chamber define a circular cross-section, each of the chambers will include a single, continuous side wall.

The mesh bottom of the growth chamber may be formed from a plastics or metal material, the mesh preferably being formed to define pores having a size in the range of 50-500 µm and more preferably in the range of 100-200 µm.

So as to prevent liquid medium overflowing from the growth chamber in circumstances where plant material located in the pores of the mesh bottom of the growth chamber has grown so as to block the pores, and thereby prevent drainage of the liquid medium via the pores, the growth chamber may include a mesh section located in the or one side wall. The mesh section is preferably formed from the same material and has the same pore size as the mesh bottom of the growth chamber, and is preferably located at or towards an edge of the side wall that is spaced from the mesh bottom.

In order to allow use of the bioreactor to produce plant biomass on a commercial scale, the growth chamber is preferably formed so as to define an inner volume in the range of 10-1,000 liters and more preferably in the range of 30-150 liters.

Preferred embodiments of the invention will now be described, by way of non-limiting examples, with reference to the accompanying drawings in which.

Figure 1:
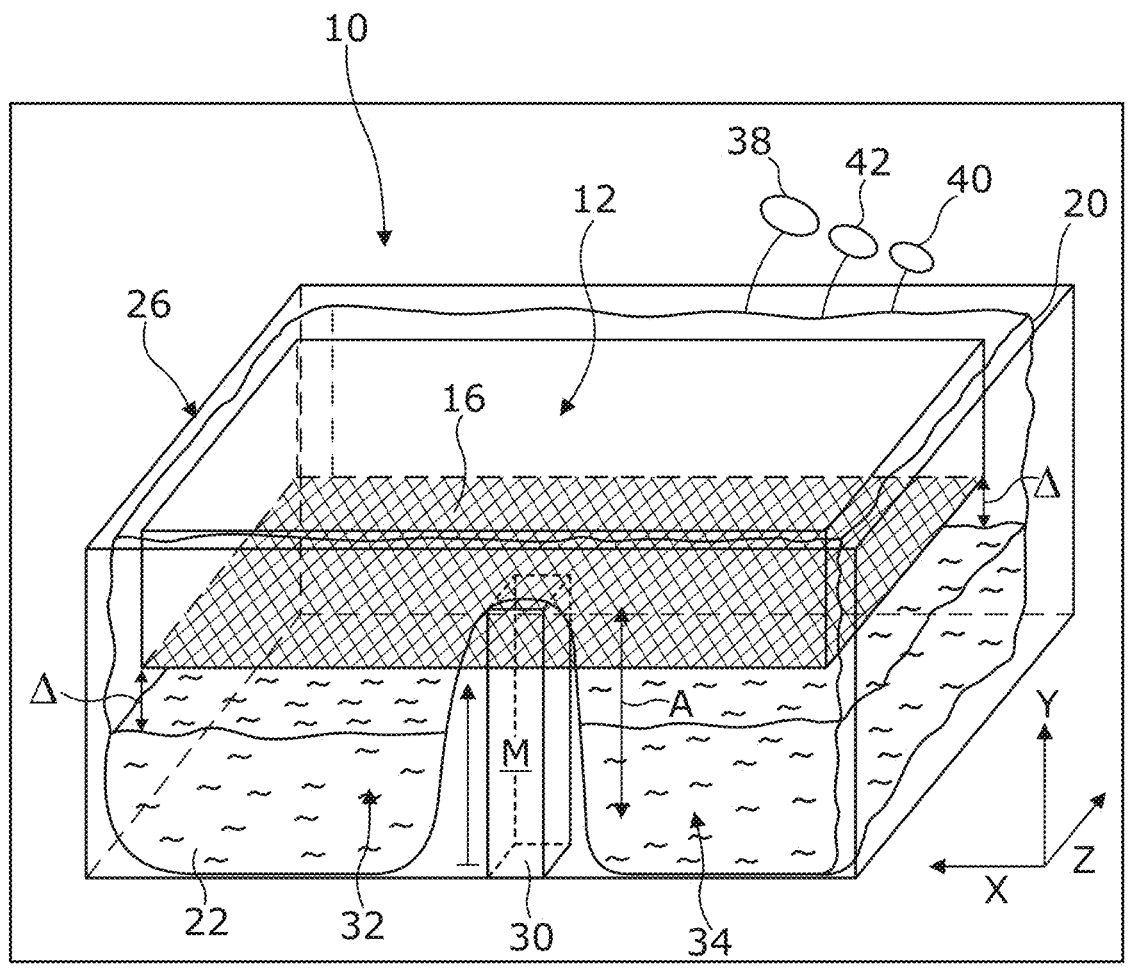
FIGS. 1 and 2 show schematic illustrations of a temporary immersion bioreactor according to a first embodiment of the invention.
Figure 2:
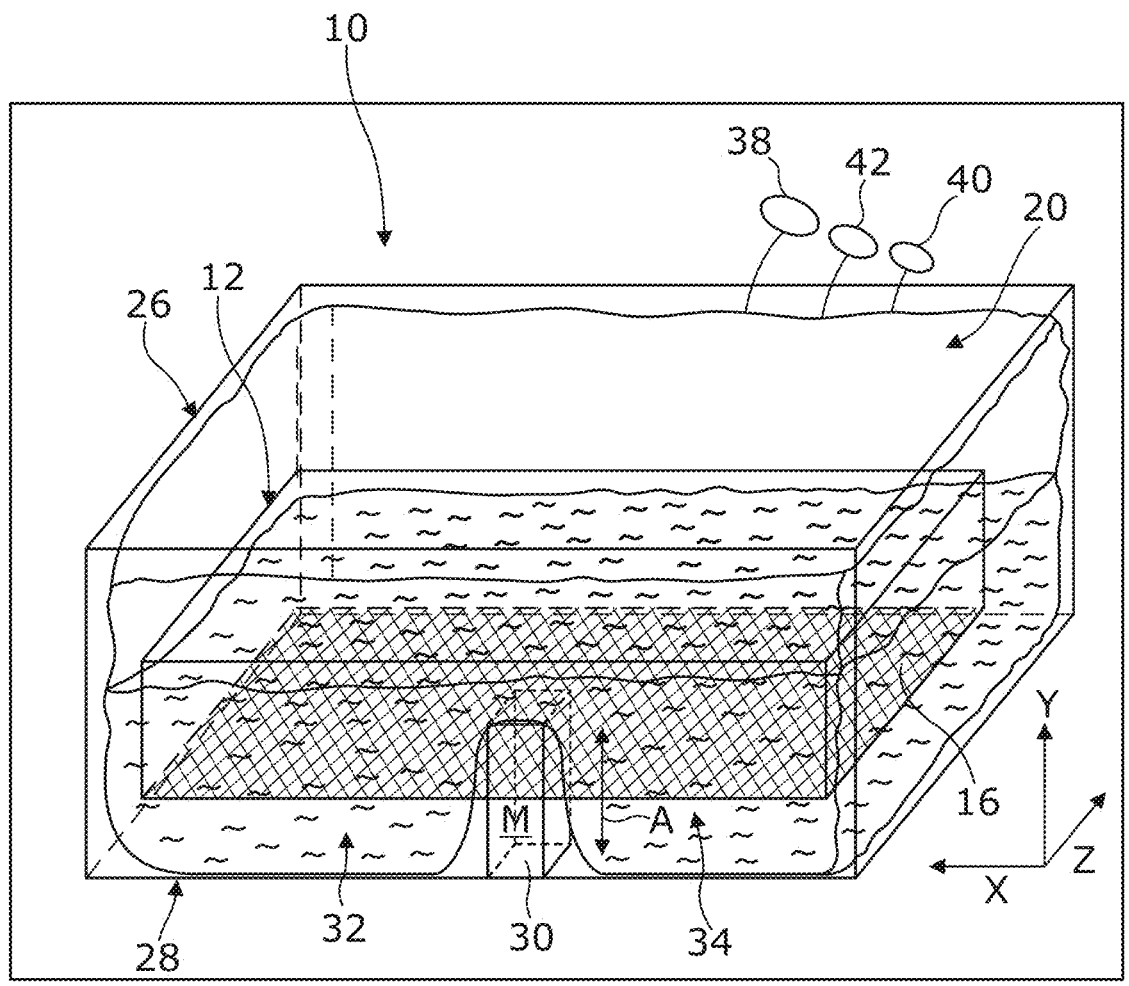

A temporary immersion bioreactor 10 for in vitro production of differentiated plant biomass, according to an embodiment of the invention, is shown in FIGS. 1 and 2.

Figure 4A:
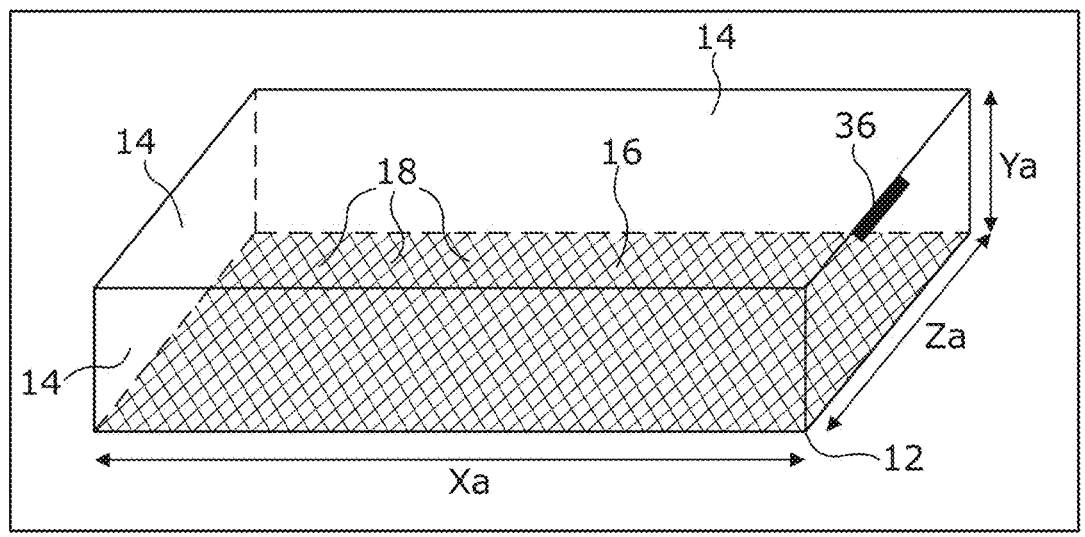
FIGS. 4a and 4b show a growth chamber of the bioreactor of FIGS. 1 and 2.
Figure 4B:
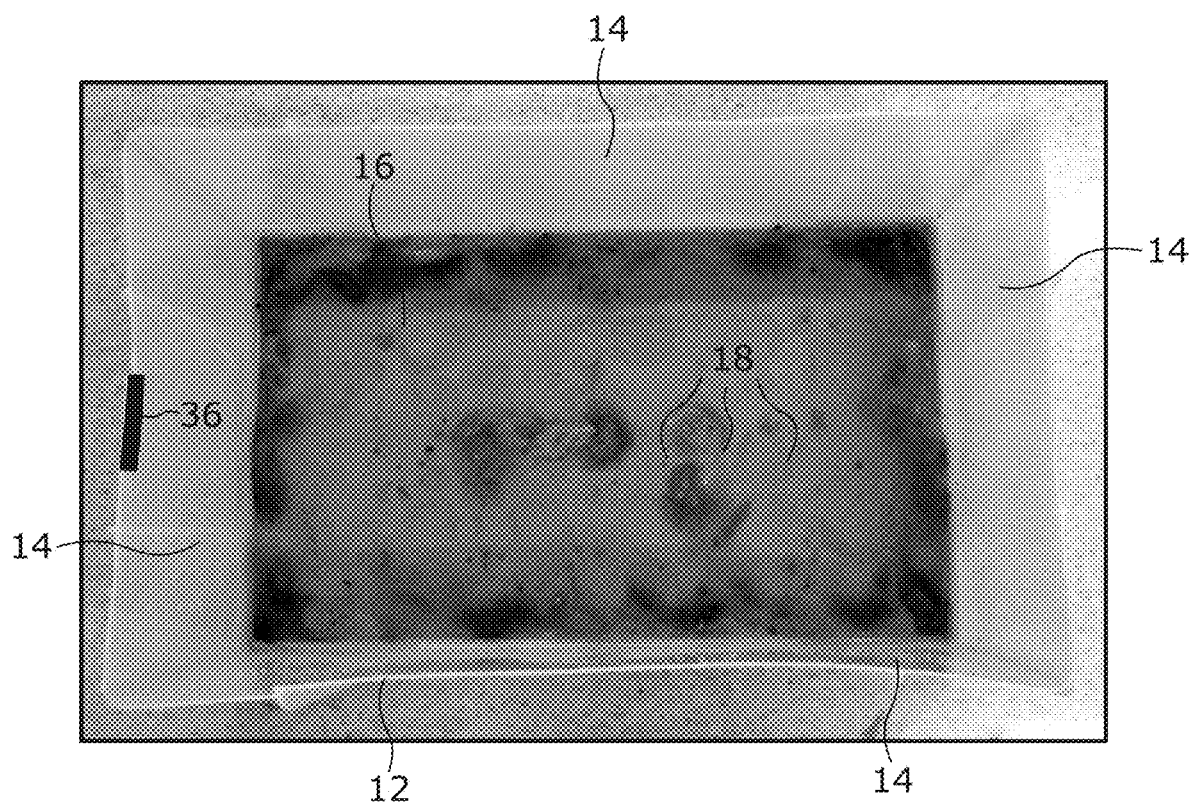

The bioreactor 10 includes a growth chamber 12 (FIGS. 4a and 4b) having a plurality of transparent side walls 14 and a mesh bottom 16 defining a plurality of pores 18 to receive plant material or inoculum. It is envisaged that the plant material or inoculum may include leaves or root pieces, cell suspensions or callus.

Figure 5A:
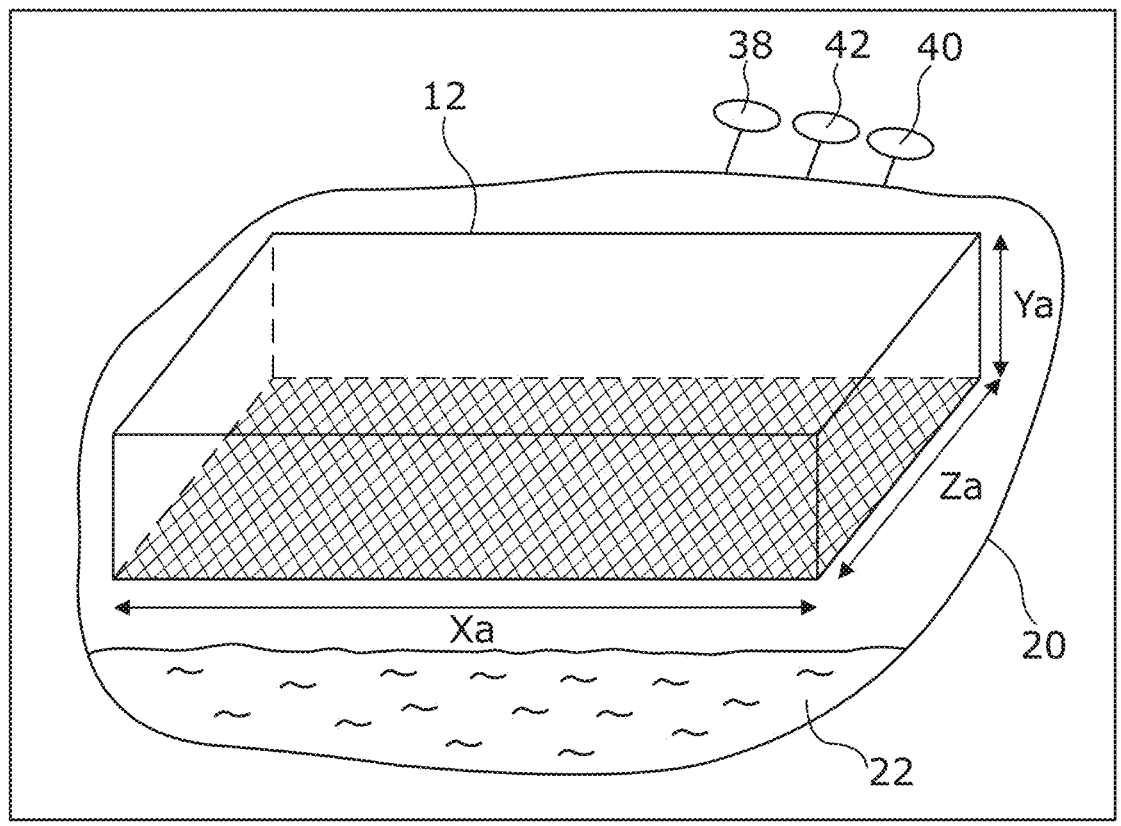
FIGS. 5a and 5b show the growth chamber and a flexible bag of the bioreactor of FIGS. 1 and 2.
Figure 5B:

The growth chamber 12 is located in a flexible bag 20 (FIGS. 5a and 5b) formed from a transparent material. The flexible bag 20 includes a sealable opening (not shown) and is dimensioned to receive the growth chamber 12 together with a liquid medium 22.

Figure 6A:
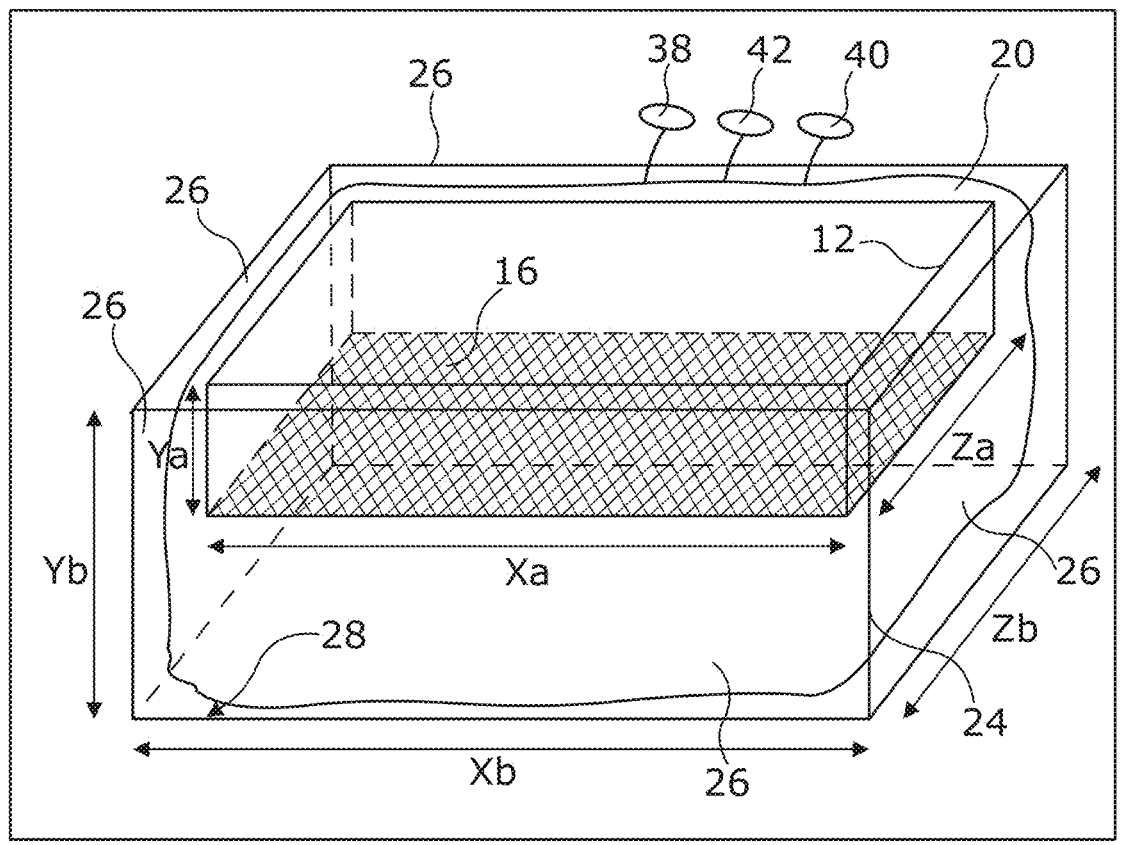
FIGS. 6a and 6b show the growth chamber, flexible bag and an outer chamber of the bioreactor of FIGS. 1 and 2.
Figure 6B:
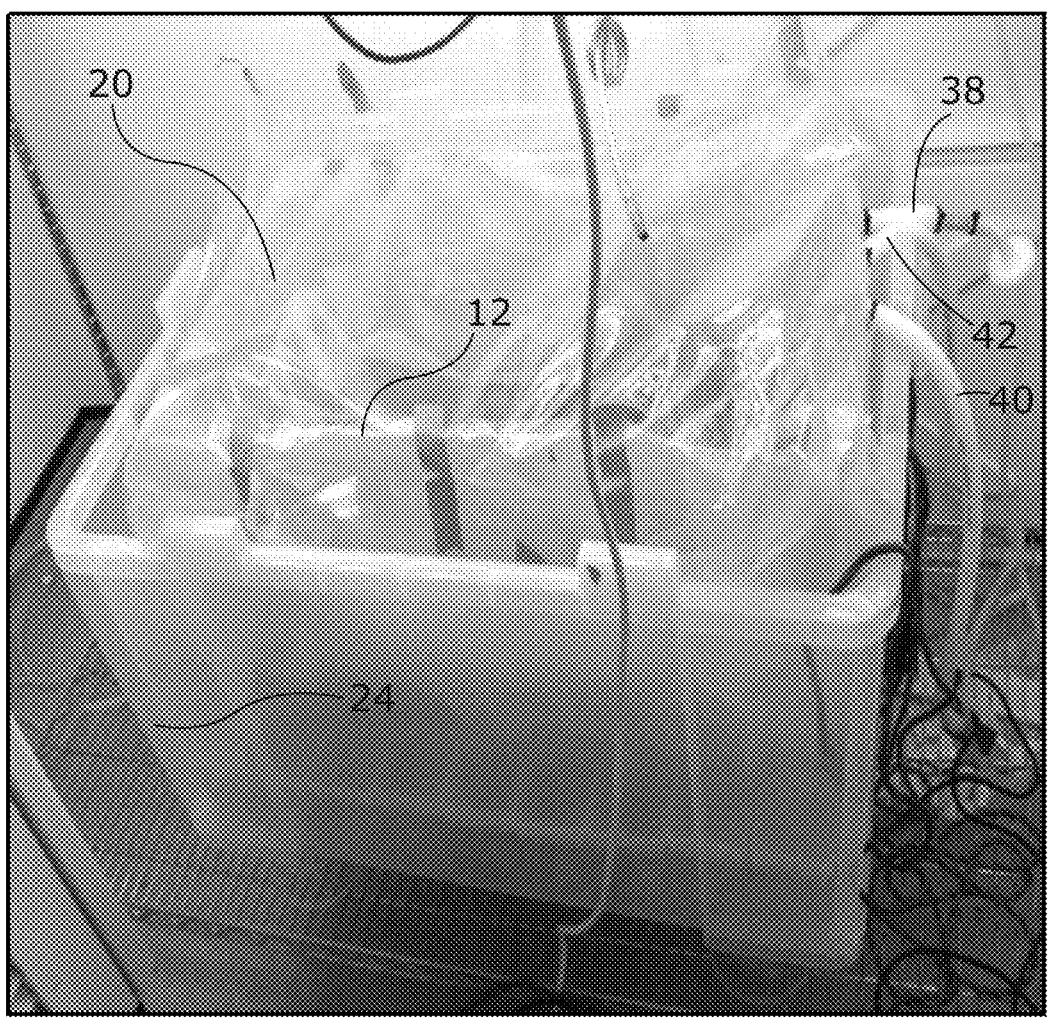

The flexible bag 20, together with the growth chamber 12 and liquid medium 22, are located in an outer chamber 24 (FIGS. 6a and 6b). The outer chamber 24 has a plurality of transparent side walls 26 and a bottom 28 that, in use, is intended to rest on a support surface.

The bioreactor 10 further includes a driving mechanism in the form of a drive arm 30 (FIGS. 1 and 2) located towards the bottom 28 of the outer chamber 24. The drive arm 30 engages an underside of the mesh bottom 16 of the growth chamber 12 via the flexible bag 20.

Figure 3:
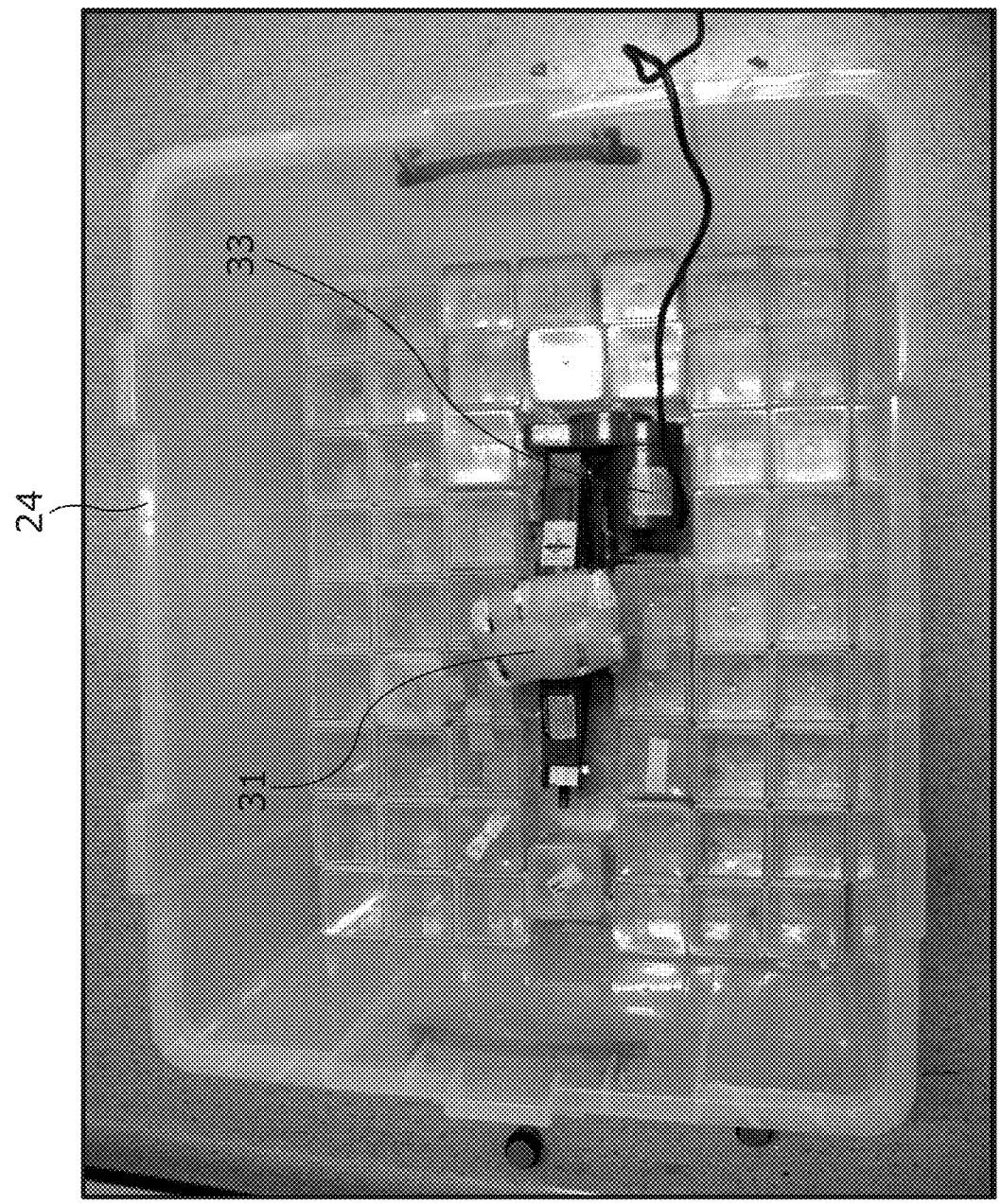
FIG. 3 shows the drive arm of the bioreactor of FIGS. 1 and 2.

Preferably the drive arm 30 is configured to present a relatively smooth engagement portion 31 (FIG. 3) that engages the underside of the mesh bottom 16 of the growth chamber 12 via the flexible bag 20. The provision of a relatively smooth engagement portion 31, having no sharp edges or protrusions, reduces the risk of the drive arm 30 tearing or otherwise rupturing the flexible bag 20.

As shown in FIGS. 1 and 2, the drive arm 30 does not engage the entire underside of the mesh bottom 16 of the growth chamber 12. The drive arm 30 engages a relatively small proportion of the underside of the mesh bottom 16 at which point the flexible bag 20 is trapped between the drive arm 30 and mesh bottom 16. As a result, two pockets 32,34 are formed on either side of the drive arm 30 into which the liquid medium 22 flows.

The growth chamber 12, the flexible bag 20 and the outer chamber 24 are each formed from a transparent material so as to allow light to penetrate and reach any plant material located in the pores 18 of the mesh bottom 16 of the growth chamber 12.

Preferably the flexible bag 20 is formed from a disposable material so as to allow disposal of the bag 20 after use.

In the embodiment shown in FIGS. 1 and 2, the flexible bag 20 is formed from polypropylene. In other embodiments, the flexible bag 20 may be formed from another flexible thermoplastic polymer such as polyethylene or polyurethane.

Locating the flexible bag 20 containing the growth chamber 12 and the liquid medium 22 in an outer chamber 24 allows the liquid medium 22 to settle within the flexible bag 20 at the bottom of the outer chamber 24, as shown in FIGS. 1 and 2. This arrangement eliminates voids forming in the liquid medium 22.

The growth chamber 12 and the outer chamber 24 are both moulded from a transparent polyethylene plastics material, so as to define a rectangular cross-section in a plane generally perpendicular to axis A.

In other embodiments the growth chamber 12 and the outer chamber 24 may be formed from plexi glass, glass or another transparent material that can withstand sterilisation by chemical, autoclaving or gamma radiation.

It is envisaged that in other embodiments the growth chamber 12 and the outer chamber 24 may be formed so as to define a different cross-sectional shape in a plane generally perpendicular to axis A. The cross-sectional shape could, for example, be circular, elliptical, triangular or square.

The growth chamber 12 of the bioreactor 10 shown in FIGS. 1 and 2 is sized so as to have a height $Y_a$ of 25 cm, a width $X_a$ of 60 cm and a depth $Z_a$ of 40 cm (the X-Y-Z axes being illustrated in FIG. 3a). This results in a growth chamber 12 having an internal volume of 60 liters.

It is envisaged that in other embodiments the width X and depth Z of the growth chamber 12 may be varied to alter the maximum internal volume of the growth chamber 12. The applicant has discovered however that the height Y of the growth chamber 12 should preferably not exceed 25 cm if sufficient light is to reach the plant material or inoculum.

The outer chamber 24 is sized so as to have a height $Y_b$ of 60 cm, a width $X_b$ of 70 cm and a depth $X_b$ of 50 cm (FIG. 6a). These dimensions allow a clearance of 5 cm on each side of the growth chamber 12 in the width X and depth Z directions when the growth chamber 12 and the flexible bag 20 are located in the outer chamber 24, as shown in FIGS. 1 and 2.

The corresponding shapes of the growth chamber 12 and the outer chamber 24, and the relative dimensions of the chambers 12,26 in the width X and depth Z directions means that the growth chamber 12 fits snugly within the side walls 28 of the outer chamber 24, thereby restraining movement of the growth chamber 12 within the outer chamber 24 to movement along a single axis A, which is essentially parallel to the height $Y_a,Y_b$ direction of the two chambers 12,26.

The bioreactor 10 shown in FIGS. 1 and 2 includes a gas pump (not shown) to create, in use, a flow of gas through the internal volume of the flexible bag 20. To facilitate connection of the air pump, the flexible bag 20 includes first and second ports 38,40 configured to define an inlet and an outlet for connection to the air pump so as to allow the flow of gas into and out of the flexible bag 20.

In use, the air pump may be activated to blow air into the sealed flexible bag 20 at the start of the bioreactor process. The air pump may then be used to renew the air in the flexible bag 20 at time intervals ranging from every 1 hour to every 6 hours, depending on the plant specifies, and preferably every 1 to 2 hours.

The volume of air pumped into the flexible bag 20 is between 2 liters per minute and 20 liters per minute, and the air is pumped from anywhere between 1 to 60 minutes each time.

The flexible bag also includes a third port 42 configured to receive liquid medium, thereby providing means for introducing the liquid medium 22 into the flexible bag 20. The third port 42 may then be used to introduce plant material or inoculum into the flexible bag 20. Preferably the amount of inoculum introduced into the flexible bag 20 is in the range of 1 to 10 g per liter of the internal volume of the growth chamber 12.

The provision of the third port 42 is advantageous in that it means that it is not necessary to seal the growth chamber 12 in the flexible bag 20 together with the liquid medium 22 or the plant material or inoculum when constructing the bioreactor 10. Introduction of the liquid medium 22 and the plant material or inoculum may be delayed until the bioreactor is fully constructed and ready for use.

This in turn means that it is only necessary to locate the third port 42 within a sterile environment during the introduction of the liquid medium 22 and/or plant material or inoculum into the bioreactor 10. It is not necessary to locate the entire bioreactor 10 within the sterile environment and accordingly the size of the sterile environment does not limit the maximum size and capacity of the bioreactor 10.

The mesh bottom 16 of the growth chamber 12 is made from stainless steel to define pores 18 having a size in the range of 50-200 μm, preferably 100 μm so as to enable them to retain the smallest cells.

The growth chamber 12 also includes a mesh section 36 located along an upper edge of a side wall 14. The mesh section 36 is also made from stainless steel and formed to define pores (not shown) corresponding in size to the pores 18 formed in the mesh bottom 16 of the growth chamber 12.

In use, the drive arm 30 is movable between a rest position in which the movable arm lies adjacent the bottom 28 of the outer chamber 24 (FIG. 2), upward along an axis A, to an extended position in which the movable arm is spaced from the bottom 28 of the outer chamber 24 (FIG. 1). As a result, the drive arm 30 drives movement of the growth chamber 12 along axis A from a first position in which the mesh bottom 16 is located towards the bottom 28 of the outer chamber 24 (FIG. 2) towards a second position in which the mesh bottom 16 is spaced from the bottom 26 of the outer chamber 28 (FIG. 1).

During movement of the drive arm 30, the pockets 32,34 formed in the flexible bag 20 on either side of the drive arm 30 increase in depth and liquid medium 22 drains from the growth chamber 12 into those pockets 32,34.

The amount of liquid medium 22 provided in the flexible bag 20 is chosen such that, when the growth chamber 12 is located in the first position, any plant material located in the pores 18 of the mesh bottom 16 of the growth chamber 12 are immersed within the liquid medium 22.

The amount of liquid medium 22 provided in the flexible bag 20 and the extended position of the drive arm 30 are preferably chosen such that, when the growth chamber 12 is located in the second position, the mesh bottom 16 of the growth chamber 12 is spaced from an upper surface of the liquid medium 22 by a distance A (FIG. 1). This ensures that the liquid medium 22 drains from the growth chamber 12. It also ensures that any plant shoots or roots protruding from the underside of the mesh bottom do not remain immersed in the liquid medium 22.

In particularly preferred embodiments the amount of liquid medium 22 provided in the flexible bag 20, and the extended position of the drive arm 30 are chosen such that the mesh bottom 16 is spaced by a distance A (FIG. 1) of at least 5 cm and preferably 10 cm from the upper surface of the liquid medium 22.

Operation of the drive arm 30 is controlled by means of a timer connected to a drive motor 33 arranged to drive movement of the drive arm 30 (FIG. 3). to the timer controls movement, in use, of the growth chamber 12 between the first and second positions and thereby controls immersion of plant material or inoculum in the liquid medium 22. By appropriate setting of the timer, it is possible to set specific periods of immersion and aeration as may be required for a particular plant material located in the pores 18 of the mesh bottom 16 of the growth chamber 12.

Figure 7:
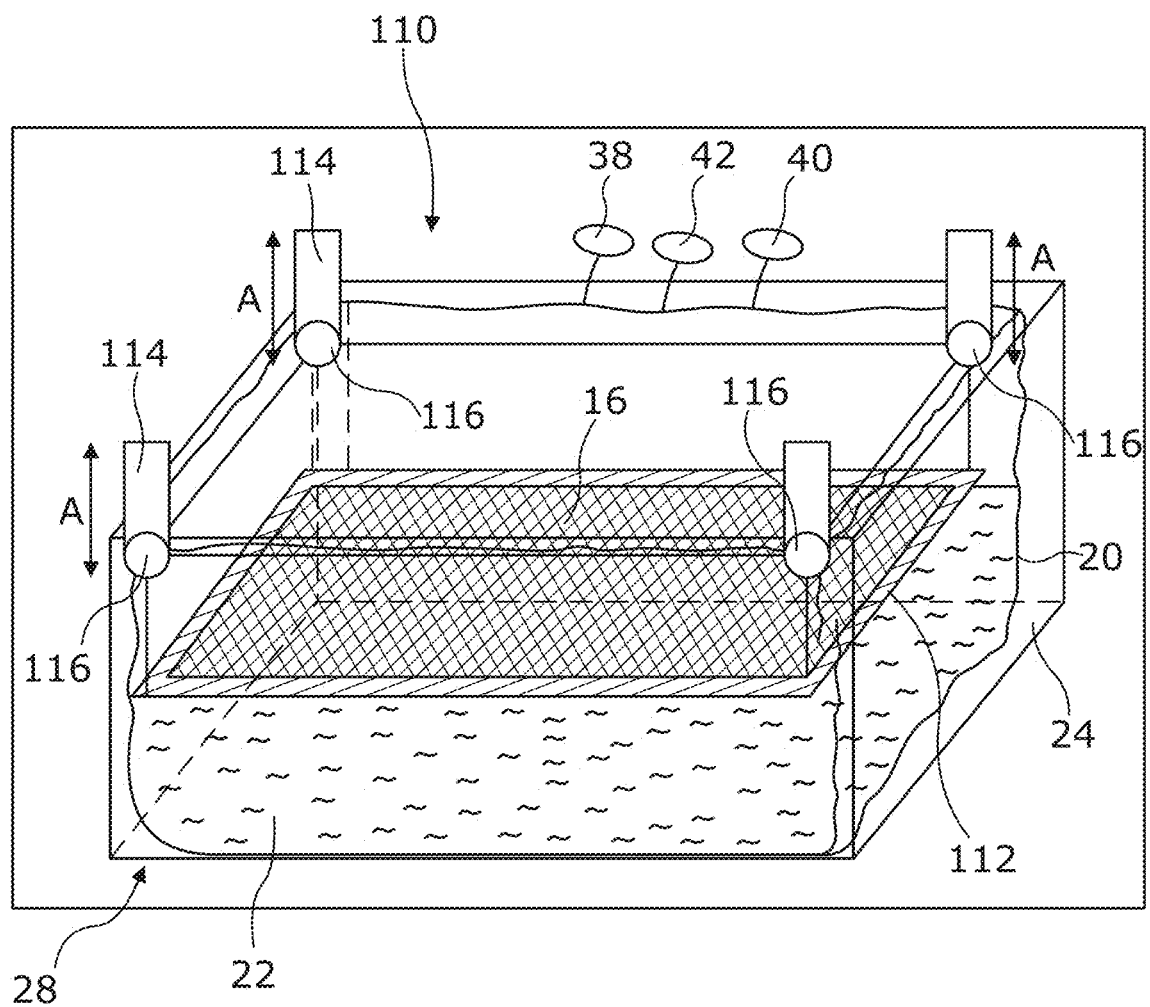
FIGS. 7 and 8 show schematic illustrations of a temporary immersion bioreactor according to a second embodiment of the invention.

A bioreactor 110 according to a second embodiment of the invention is shown in FIGS. 6 and 7.

The structure of the bioreactor 110 is very similar to the structure of the bioreactor 10 shown in FIGS. 1 and 2. Those features common to both embodiments are referred to using the same reference numerals and will not be described again in detail.

Figure 8:
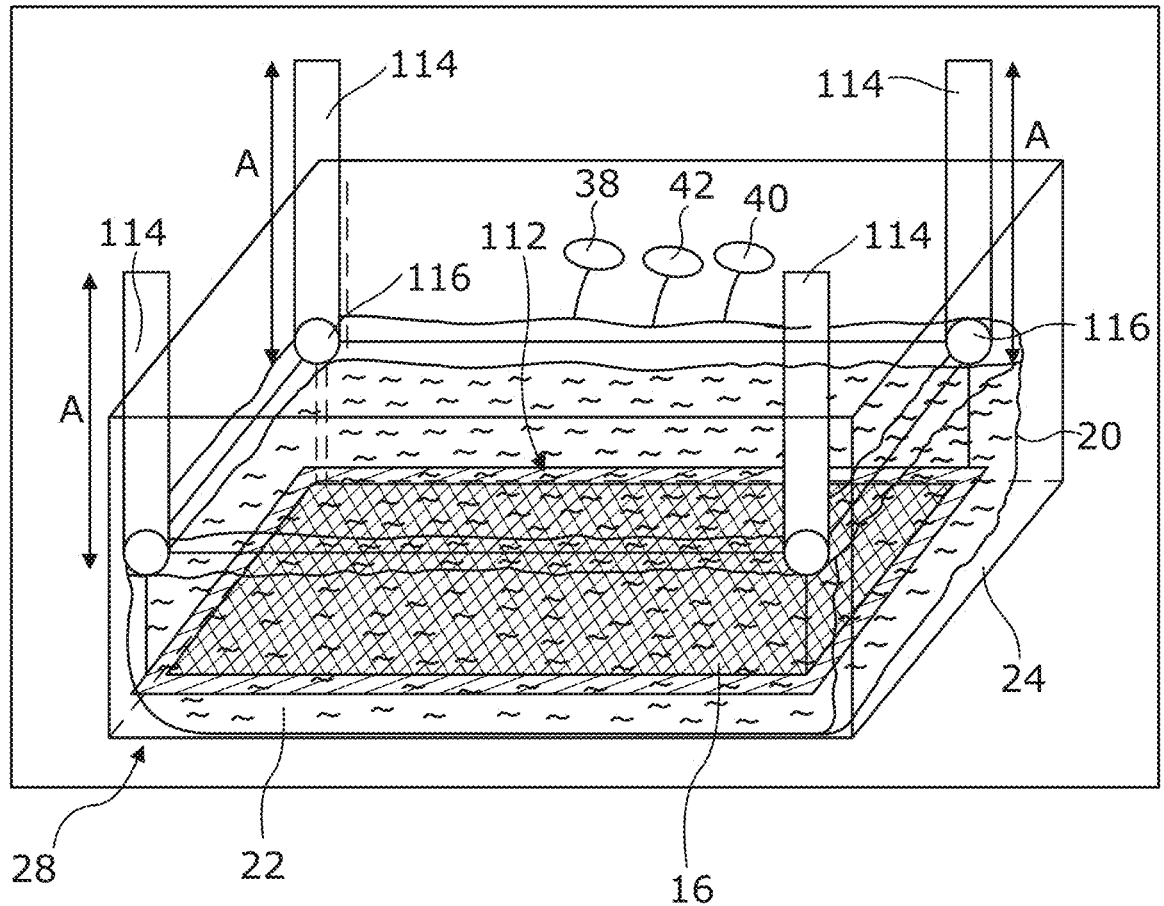

The bioreactor 110 shown in FIGS. 7 and 8 differs from the bioreactor 10 shown in FIGS. 1 and 2 in that it omits a drive arm 30 to drive movement of the growth chamber 12 from the first position to the second position.

In the embodiment shown in FIGS. 7 and 8, the growth chamber 12 includes a float element 112 mounted so as to extend around the mesh bottom 16 of the growth chamber 12.

The float element 112 permits the growth chamber 12 to float, in use, on the liquid medium contained in the flexible bag 20 and thereby locate the growth chamber 12 in the second position (FIG. 7) where the mesh base 16 is spaced from the bottom 28 of the outer chamber 24.

In the embodiment shown in FIGS. 7 and 8, the float element 112 has a depth of 10 cm so that, when the growth chamber 12 floats on the liquid medium 22, the mesh bottom 16 of the growth chamber 12 is spaced by a distance A of 10 cm from the surface of the liquid medium 22.

So as to immerse the growth chamber 12 in the liquid medium 22 when required, the bioreactor 110 includes four plungers 114 located in the outer chamber 24. The plungers 114 are arranged so that engagement members 116 provided on the plungers 114 engage upper edges of the growth chamber 12.

In use, each plunger 114 is operable to selectively drive the respective engagement member 116 downward along the axis A from a rest position to an extended position so as to drive movement of the growth chamber 12 from the second position to the first position where the mesh bottom of the growth chamber 12 is immersed in the liquid medium 22 (FIG. 8).

Following immersion of the mesh bottom 16 of the growth chamber 12 in the liquid medium 22, each of the plungers 114 is operable to selectively drive the respective engagement member 116 upward along the axis A from the extended position to the rest position and thereby guide movement of the growth chamber 12 upwards from the first position to the second position under the action of the float member 112.

Operation of the plungers 114 is controlled by means of a timer so as to control movement, in use, of the growth chamber 12 between the first and second positions and thereby control immersion of plant material or inoculum in the liquid medium 22. By appropriate setting of the timer, it is possible to set specific periods of immersion and aeration as may be required for a particular plant material located in the pores 18 of the mesh bottom 16 of the growth chamber 12.

In one particular method of operation of the bioreactor 10 shown in FIGS. 1 and 2 or the bioreactor 110 shown in FIGS. 7 and 8, the bioreactor 10,110 is located in a controlled environment at 25° C., with a 16 hour/8 hour day/night cycle and a light intensity of 50 $\mu Molm^{-2}s^{-1}$ at the bag level.

The inoculum is introduced into the flexible bag 20 via the third port 42. Thereafter 50 liters of liquid medium 22 are introduced into the flexible bag 20 such that the liquid medium 22 covers 80% of the growth chamber 12 when the growth chamber 12 is immersed in the liquid medium 22 within the flexible bag 20.

Starting the bioreactor process with the growth chamber 12 in the second position, spaced from the bottom 28 of the outer chamber 24, the liquid medium 22 flows through the mesh bottom 16 of the growth chamber 12 so as to collect at the bottom of the flexible bag 20 within the outer chamber 24.

The air pump is connected to the first port 38 to pump ambient air into the flexible bag 20 at a rate of 15 liters per minute over a period of 10 minutes each hour. In other embodiments, the air may be enriched with up to 1% of carbon dioxide.

The timer is set to immerse the growth chamber 12 in the liquid medium 22 for a period of 4 minutes every 6 hours.

Figure 9:
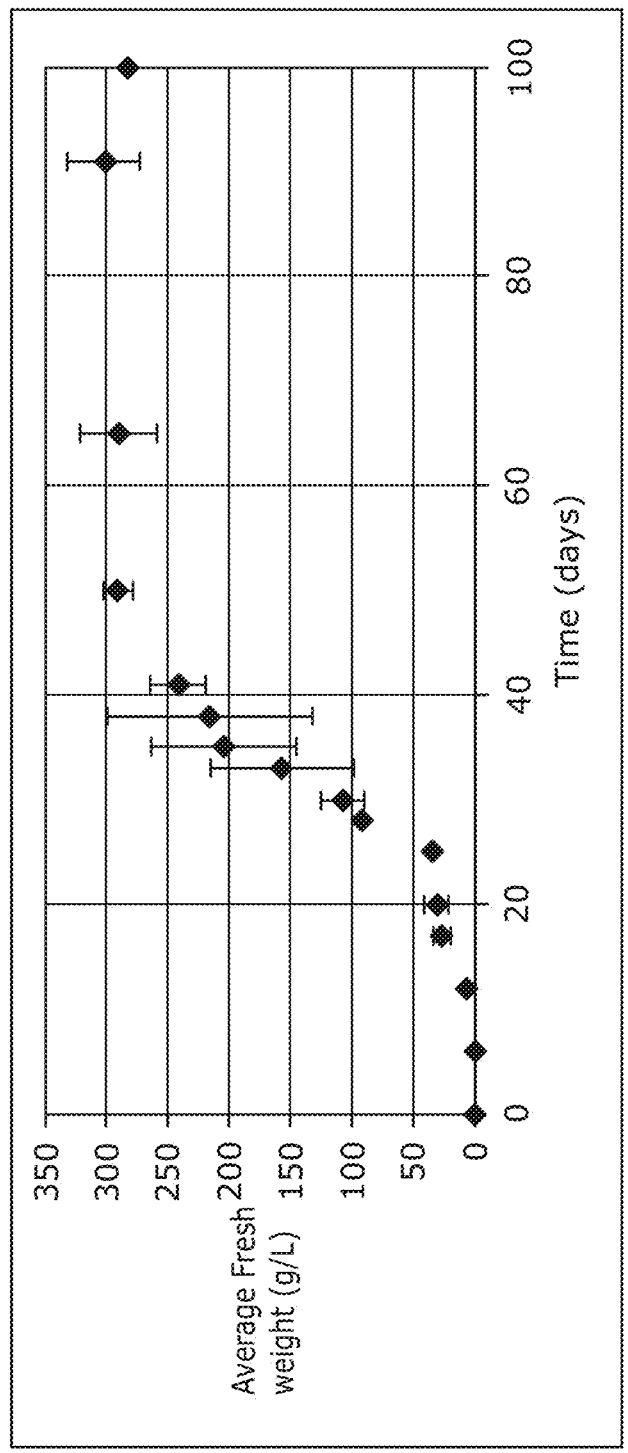
FIG. 9 illustrates the rate of growth of leafy biomass using the bioreactor of FIGS. 1 and 2.
Figure 10:
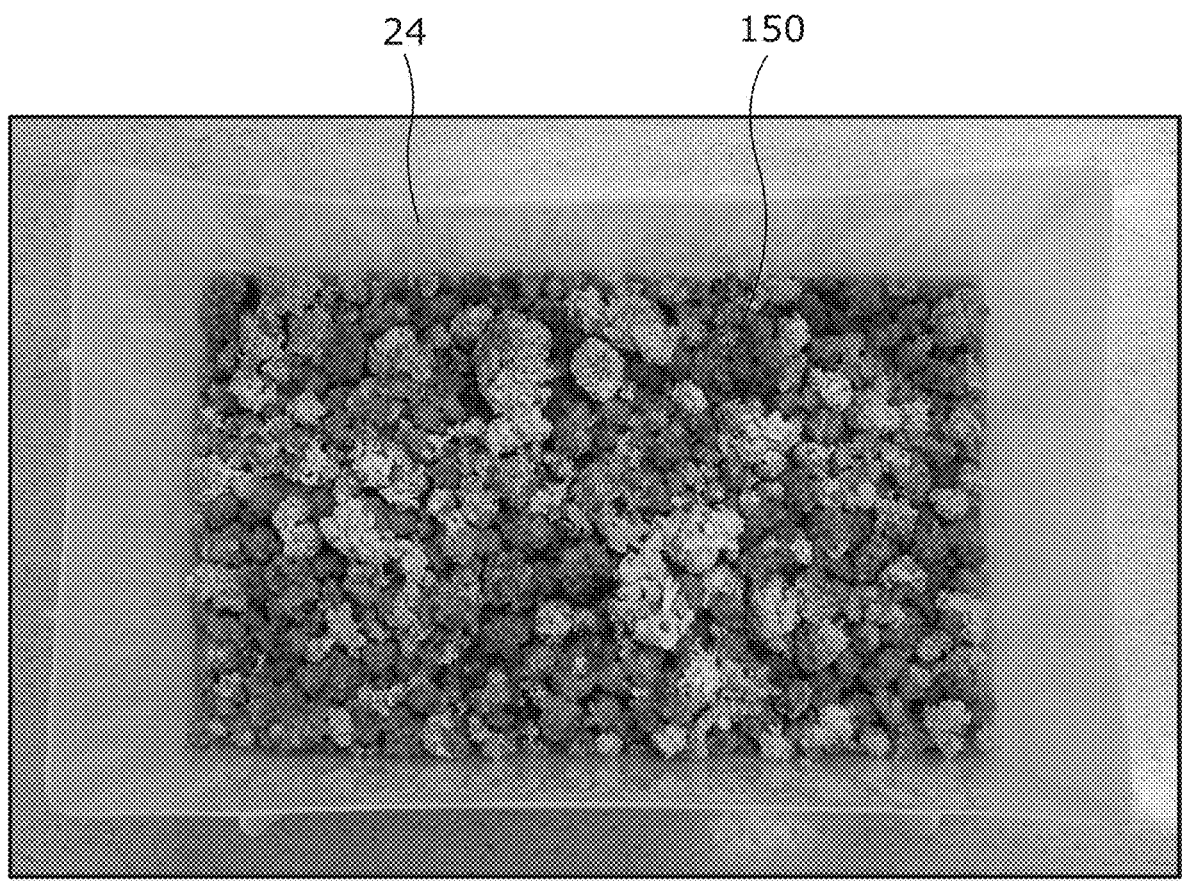
FIG. 10 shows leafy biomass of *Nicotiana tabacum* produced using the bioreactor of FIGS. 1 and 2.

Following this mode of operation, the growth of biomass becomes exponential after a lag period of 3 weeks (as illustrated in FIG. 9) until it reaches a plateau after 50 days. The maximal biomass yield is estimated at about 300 g f.w./L (fresh weight per liter).

Leafy biomass of *Nicotiana tabacum* is shown by way of illustrative example of the biomass 150 that may be produced through use of the bioreactor 10 in accordance with the method outlined above.

The invention claimed is:

1. A temporary immersion bioreactor for in vitro production of differentiated plant biomass, the temporary immersion bioreactor comprising:
    a growth chamber having one or more transparent side walls and a mesh bottom, the mesh bottom defining a plurality of pores to receive plant material;
    an outer chamber having one or more transparent side walls, the outer chamber being formed to correspond in shape to the growth chamber so that the mesh bottom of the growth chamber faces a bottom of the outer chamber that in use is intended to rest on a support surface and movement of the growth chamber within the outer chamber is restrained to movement along a single axis such that the mesh bottom of the growth chamber moves towards and away from the bottom of the outer chamber;
    a flexible bag formed from a transparent material and the flexible bag is located in the outer chamber, the flexible bag having a sealable opening and containing the growth chamber and a liquid medium; and a drive arm located in the outer chamber so as to engage an underside of the mesh bottom of the growth chamber wherein the drive arm is arranged to selectively drive movement of the growth chamber along a single axis, when the growth chamber and the flexible bag are received in the outer chamber, between a first position in which the mesh bottom of the growth chamber is located at or towards the bottom of the outer chamber and a second position in which the mesh bottom of the growth chamber is spaced from the bottom of the outer chamber.

2. The temporary immersion bioreactor according to claim 1 wherein the flexible bag further includes a sealable port to receive liquid medium and/or inoculum therethrough.

3. The temporary immersion bioreactor according to claim 1 further including an air pump for connection to the flexible bag so as to allow a gas to be conveyed through the flexible bag.

4. The temporary immersion bioreactor according to claim 3 wherein the flexible bag includes at least three ports, first and second ports being configured for connection to the air pump to allow the flow of gas into and out of the flexible bag and a third port configured to receive liquid medium and/or inoculum therethrough.

5. The temporary immersion bioreactor according to claim 1 wherein the drive arm being movable in a first direction along the single axis upwards from the bottom of the outer chamber to an extended position so as to push the growth chamber from the first position to the second position, and the drive arm being movable from the extended position in a second, opposite direction along the single axis so as to guide movement of the growth chamber downwards from the second position to the first position.

6. The temporary immersion bioreactor according to claim 1 wherein the drive arm includes a float element mounted so as to extend around the mesh bottom of the growth chamber and thereby allow the growth chamber to float on a liquid medium contained in the flexible bag when the growth chamber and flexible bag are received in the outer chamber and thereby locate the growth chamber in the second position, and the drive arm further including one or more drive elements provided in the outer chamber to selectively engage the growth chamber and drive movement of the growth chamber from the second position to the first position.

7. The temporary immersion bioreactor according to claim 6 wherein the float element has a depth of at least 5 cm so that, when the growth chamber floats on a liquid medium, the mesh bottom of the growth chamber is spaced at least 5 cm from the liquid medium.

8. The temporary immersion bioreactor according to claim 7 wherein the floatation element has a depth of 10 cm.

9. The temporary immersion bioreactor according to claim 6 wherein the drive arm includes one or more drive elements in the form of a plunger located within the outer chamber, the or each plunger having an engagement member to engage an upper edge of the or at least one side wall of the growth chamber, via the flexible bag, when the growth chamber and the flexible bag are received in the outer chamber, the or each plunger being movable to drive movement of the respective engagement member from a rest position at the top of the outer chamber, in the first direction towards the extended position, and thereby drive movement of the growth chamber from the second position to the first position, and the or each plunger being movable to drive movement of the respective engagement member from the extended position in a second, opposite direction along the single axis so as to guide movement of the growth chamber from the first position to the second position under the action of the float member or opposing electro-magnets.

10. The temporary immersion bioreactor according to claim 9 wherein the drive arm includes at least three such plungers located within the outer chamber at equidistantly spaced locations about an inner circumference of the outer chamber.

11. The temporary immersion bioreactor according to claim 6 wherein the drive arm includes at least two drive elements located within the outer chamber, towards the bottom of the outer chamber.

12. The temporary immersion bioreactor according to claim 1 wherein the drive arm further comprises one or more drive elements provided in the outer chamber to selectively engage the growth chamber and drive movement of the growth chamber in a second, opposite direction along the single axis from the second position to the first position.

13. The temporary immersion bioreactor according to claim 1 wherein the drive arm includes a timer to control operation of the drive arm and thereby, in use, control movement of the growth chamber between the first and second positions.

14. The temporary immersion bioreactor according to claim 1 wherein the flexible bag is formed from a flexible thermoplastic polymer.

15. The temporary immersion bioreactor according to claim 14 wherein the flexible bag is formed from polypropylene, polyethylene or polyurethane.

16. The temporary immersion bioreactor according to claim 1 wherein the cross-sectional shapes of the growth chamber and the outer chamber, in a plane generally perpendicular to the single axis, are the same, the cross-sectional shape being selected from circular, elliptical, square, triangular or rectangular.

17. The temporary immersion bioreactor according to claim 1 wherein the mesh bottom of the growth chamber is formed to define pores having a size in the range of 50-500 µm.

18. The temporary immersion bioreactor according to claim 17 wherein the mesh bottom of the growth chamber is formed to define pores having a size in the range of 100-200 µm.

19. The temporary immersion bioreactor according to claim 1 wherein the growth chamber includes a mesh section located in the or one side wall, at or towards an opposite edge from the mesh bottom, the mesh bottom and the mesh section being formed from the same material and having the same pore size as the mesh bottom of the growth chamber.

20. The temporary immersion bioreactor according to claim 1 wherein the growth chamber is formed so as to define an inner volume in the range of 10-1,000 liters.

21. The temporary immersion bioreactor according to claim 20 wherein the growth chamber is formed so as to define an inner volume in the range of 30-150 liters.

* * * * *